United States Patent
Ostrow

(10) Patent No.: US 8,260,408 B2
(45) Date of Patent: Sep. 4, 2012

(54) POST-EXERCISE ARRHYTHMIA DETECTION

(75) Inventor: Eliot L. Ostrow, Sunnyvale, CA (US)

(73) Assignee: Pacesetter, Inc., Sylmar, CA (US)

( * ) Notice: Subject to any disclaimer, the term of this patent is extended or adjusted under 35 U.S.C. 154(b) by 709 days.

(21) Appl. No.: 12/492,055

(22) Filed: Jun. 25, 2009

(65) Prior Publication Data

US 2010/0331713 A1    Dec. 30, 2010

(51) Int. Cl.
  *A61B 5/0452*    (2006.01)
  *A61B 5/0464*    (2006.01)
(52) U.S. Cl. ......... 600/515; 600/517; 600/518; 600/519
(58) Field of Classification Search .................. 600/508, 600/522, 517, 515, 519, 518, 520; 607/9, 607/17
See application file for complete search history.

(56) References Cited

OTHER PUBLICATIONS

Dewey, Frederick E. BA et al., "Ventricular Arrhythmias During Clinical Treadmill Testing and Prognosis," Arch Intern Med. 2008;168(2):225-234.

*Primary Examiner* — Carl H. Layno
*Assistant Examiner* — Jon-Eric C. Morales

(57) ABSTRACT

Post-exercise arrhythmias are detected by an implantable medical device. In some aspects, post-exercise arrhythmia may be prognostic of a worsening cardiovascular condition. Thus, the detection of post-exercise arrhythmia may be used as an indicator for adjusting the therapy prescribed for a patient. In some aspects post-exercise arrhythmia are detected if a patient is exercising at a level that equals or exceeds a threshold exercise level. In some aspects, therapy for a patient is modified if the detected post-exercise arrhythmia exceeds a threshold arrhythmia level. In some aspects therapy for a patient is modified if ischemia is detected in conjunction with post-exercise arrhythmia.

18 Claims, 7 Drawing Sheets

POST-EXERCISE ARRHYTHMIA DETECTION

TECHNICAL FIELD

This application relates generally to implantable cardiac devices and, more specifically, but not exclusively to detecting post-exercise arrhythmia.

BACKGROUND

An implantable device, such as an implantable cardiac rhythm management device (e.g., a pacemaker, a defibrillator, or a cardioverter), may be used to monitor cardiac function and provide therapy for a patient who suffers from cardiac arrhythmia. For example, in an attempt to maintain regular cardiac rhythm, the implantable device may track the type and timing of native cardiac signals. In this way, the implantable device may determine whether cardiac events (e.g., contractions) are occurring and whether they are occurring at the proper times.

The implantable device may track cardiac signals through the use of one or more leads implanted in or near the heart of the patient. For example, the implantable device may process signals received via implanted leads and then attempt to characterize the received signals as a particular cardiac event. Such cardiac events may include, for example, P-waves, R-waves, T-waves, or arrhythmia events.

By analyzing the type and timing of these cardiac events, the implantable device may determine whether therapy should be provided and, if so, the type of therapy to be provided (e.g., stimulation pulses). For example, if the implantable device detects desired cardiac events at the appropriate relative times, the device may simply continue monitoring for cardiac events.

In contrast, if arrhythmias are detected (e.g., cardiac events are not occurring at appropriate times or undesired cardiac events are detected), the implantable device may stimulate the heart in an attempt to restore normal cardiac rhythm. For example, in some cases, if a particular cardiac event has not been detected for a defined period of time, the implantable device may deliver an appropriate stimulation (e.g., pacing) pulse to the one or more chambers of the heart to make up for the missing cardiac event. Similarly, in cases where too many cardiac events of a given type are received over a defined time period (e.g., a tachycardia condition is detected), the implantable device may deliver electrical pulses via one or more implanted leads in an attempt to restore normal cardiac rhythm.

An implantable device also may be used to adapt therapy in other ways. For example, in some cases an implantable device may send data representative of the detected cardiac events to an external device (e.g., a home monitor). In this way, a treating physician may adjust the patient's therapy (e.g., prescribe a different drug, different amounts of a drug, or different stimulation parameters) based on the detected cardiac events.

In practice, not all arrhythmias are prognostic of worsening cardiac function. Thus, the detection of arrhythmias may not necessarily indicate that a change in therapy is warranted. Accordingly, a need exists for effective techniques for identifying arrhythmias that are indicative of a change in a patient's condition.

SUMMARY

A summary of several sample aspects of the disclosure follows. For convenience, a particular aspect or several aspects of the disclosure may be referred to herein using terminology such as "in some aspects."

The disclosure relates in some aspects to detecting post-exercise arrhythmias through the use of an implantable device. In some aspects, post-exercise arrhythmia may be prognostic of a worsening cardiovascular condition. Thus, the detection of post-exercise arrhythmia may be used as an indicator for prescribing therapy for a patient.

The disclosure relates in some aspects to detecting post-exercise arrhythmia if a patient is exercising (i.e., involved in bodily exertion) at or above a threshold exercise level. Here, the threshold exercise level may correspond to an amount of exercise that is likely to result in post-exercise arrhythmia that is particularly prognostic of a given medical condition (e.g., cardiovascular mortality). Thus, once this level of exercise is detected, arrhythmia monitoring may be invoked for a period of time after the exercise ends.

The disclosure relates in some aspects to modifying therapy for a patient if the detected post-exercise arrhythmia exceeds a threshold arrhythmia level. Here, the threshold arrhythmia level may correspond to an arrhythmia that is particularly prognostic of a given medical condition. If such an arrhythmia is detected, the implantable device generates an appropriate indication of the arrhythmia. For example, the implantable device may generate an alert or the implantable device may send information indicative of the arrhythmia to an external device (e.g., a home monitor). An attending physician may then alter the patient's therapy, if appropriate, based on the generated indication.

The disclosure relates in some aspects to determining appropriate therapy for a patient based on whether ischemia is detected in conjunction with post-exercise arrhythmia. For example, an implantable device may monitor the ischemic condition of a patient at the same time that post-exercise arrhythmia is monitored. In this case, an attending physician may alter the patient's therapy based on an indication of the ischemic condition and the post-exercise arrhythmia provided by the implantable medical device.

BRIEF DESCRIPTION OF THE DRAWINGS

These and other features, aspects, and advantages will be more fully understood when considered with respect to the following detailed description, the appended claims, and the accompanying drawings, wherein:

Figure 1:
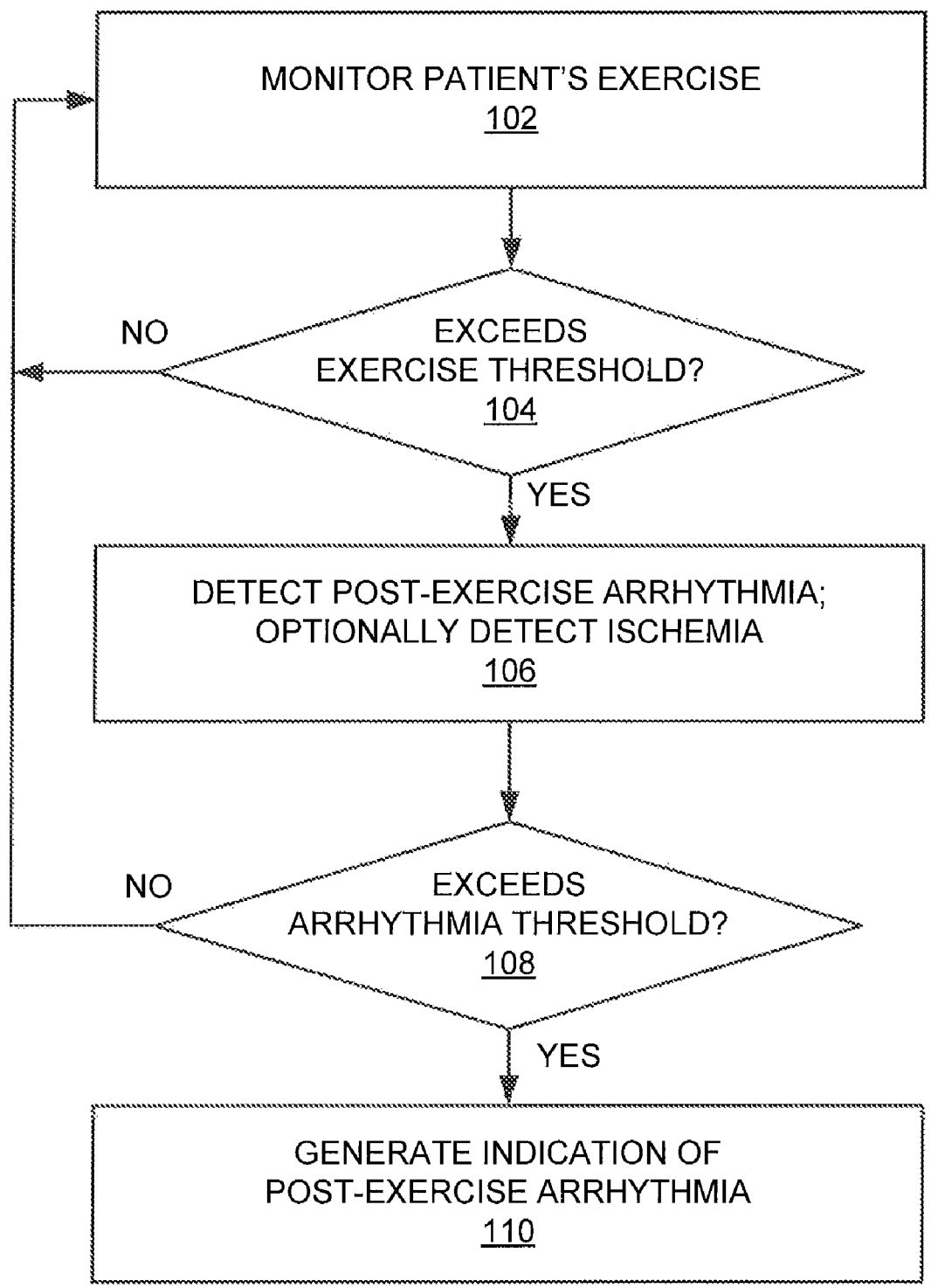
FIG. 1 is a simplified flowchart of an embodiment of operations that may be performed to detect post-exercise arrhythmia.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates sample operations that may be performed (e.g., by an implantable device) in conjunction with detecting post-exercise arrhythmias. Briefly, these operations involve determining whether a patient is exercising, detecting any arrhythmia that occurs after the patient stops exercising, and generating an indication of post-exercise arrhythmia, as appropriate.

Figure 2:
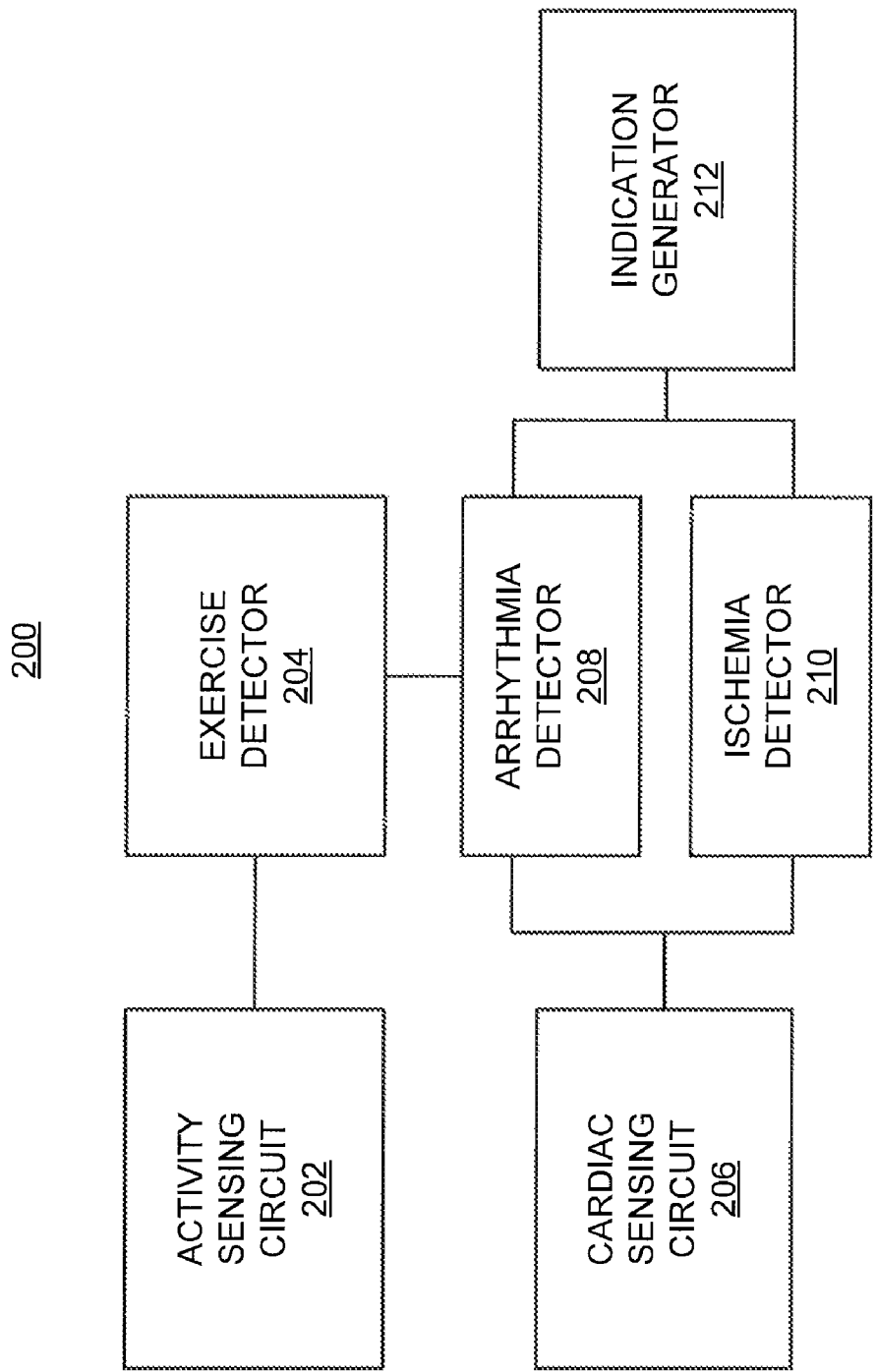
FIG. 2 is a simplified block diagram of an embodiment of an apparatus configured to detect post-exercise arrhythmia.

For convenience, the operations of FIG. 1 (or any other operations discussed or taught herein) may be described as being performed by specific components (e.g., the components of an apparatus 200 of FIG. 2). It should be appreciated, however, that these operations may be performed by other types of components and may be performed using a different number of components. It also should be appreciated that one or more of the operations described herein may not be employed in a given implementation.

As represented by blocks 102 and 104 of FIG. 1, one or more physiologic conditions of a patient are monitored over time to determine whether the patient is exercising at or above a defined exercise threshold. The exercise threshold may be defined based on a determination that a certain level of exercise by a patient (e.g., resulting from the patient engaging in relatively strenuous activity) may be prognostic of post-exercise arrhythmias. In addition, the exercise threshold may be defined based on a determination that a certain level of exercise by a patient may be prognostic of post-exercise arrhythmias that are, in turn, prognostic of a certain cardiac condition of the patient (e.g., prognostic of cardiovascular mortality).

In the example of FIG. 2, the monitoring of block 102 is performed by an activity sensing circuit 202 that acquires physiologic signals that serve to indicate whether a patient is exercising and, in some cases, indicate the intensity of the exercise. The activity sensing circuit 202 may take various forms. For example, the activity sensing circuit 202 may include one or more sensors for detecting (e.g., directly determining or indirectly estimating) one or more of acceleration, heart rate, motion, respiration, catecholamine levels, stress, or some other suitable activity-related physiologic function that is indication of exercise. Thus, in some implementations the activity sensing circuit 202 may comprise one or more accelerometers for measuring acceleration or other motion by the patient. In some implementations the activity sensing circuit 202 may comprise heart rate detection circuitry (e.g., based on detected cardiac electrical signals, pressure signals, etc.). In some implementations the activity sensing circuit 202 may comprise respiration detection circuitry (e.g., that measures thoracic impedance, detects cardiac electrical signals, etc.). In some implementations the activity sensing circuit 202 may comprise QT interval detection circuitry (e.g., for estimating a stress level of a patient).

The activity sensing circuit may be located in different locations within the patient in different implementations. In some cases at least a portion of the activity sensing circuit 202 may be implemented within the housing of an implantable device (e.g., a pacemaker). In some cases at least a portion of the activity sensing circuit 202 may be implemented within an implantable lead.

In FIG. 2 the comparison of block 104 is performed by an exercise detector 204. Initially, the exercise detector 204 may process signals received from one or more sensors or other circuits of the activity sensing circuit 202 to determine one or more exercise-related quantities that are indicated by the signals. For example, the exercise detector 204 may quantify the amplitude and/or frequency of any detected acceleration, determine the heart rate and/or respiration rate of the patient, and so on.

The exercise detector 204 may then compare each exercise-related quantity with a corresponding exercise threshold. For example, in some cases the operations of block 104 may involve comparing measured accelerometer counts (e.g., corresponding to amplitude and/or frequency) with one or more corresponding thresholds. In some cases the operations of block 104 may involve comparing a measured heart rate with a target heart rate (e.g., a certain percent of a maximum predicted heart rate), or may involve comparing a measured respiration rate with a target respiration rate, and so on.

In some cases the operations of block 104 may involve determining whether a patient has exercised at or above a certain level for a given period of time. For example, the exercise detector 204 may determine whether a patient's heart rate has exceeded a defined rate for a defined period of time.

In some cases the operations of block 104 may take into account multiple exercise-related quantities. For example, in the event measured heart rate meets or exceeds a defined rate threshold, the exercise detector 204 also may verify whether measured acceleration meets or exceeds a defined acceleration threshold, since an increase in heart rate may not necessarily indicate that the patient is exercising. A heart rate over a given threshold in combination with an acceleration reading over a given threshold may, however, provide a reliable indicator of exercise. Similarly, an increase in respiration rate or catecholamine levels may be used to substantiate whether the patient is exercising.

As represented by block 106 of FIG. 1, if the patient is exercising at a sufficient intensity and/or for a sufficient duration, arrhythmia monitoring is invoked during a post-exercise time period. For example, cardiac signals may be monitored to determine the type, quantity, and severity (e.g., magnitude) of any arrhythmia that occurs within several minutes of the end of exercise. Here, the acquisition and storage of electrograms may be triggered based on one or more fixed or selectable criteria to identify the presence of a post-exercise arrhythmia. For example, storage may be triggered based on the detection of exercise, the detection of arrhythmia, the detection of ischemia, some other factor, or a combination of these factors.

Various types of arrhythmias that are prognostic of a cardiac condition may be detected here. For example, in some cases premature ventricular contractions ("PVCs") that occur during a post-exercise period may be prognostic of a cardiac condition. Here, PVCs may relate to single PVCs, PVC couplets, PVT triplets, etc. Other examples of arrhythmias include sustained ventricular tachycardia ("VT"), non-sustained VT, premature atrial contractions, and atrial fibrillation.

Referring again to the example of FIG. 2, the exercise detector 204 may detect the end of exercise based on analysis of the signals from the activity sensing circuit 202 (e.g., an exercise-related quantity falls below a threshold level). The exercise detector 204 may then send an indication of the end of exercise to an arrhythmia detector 208. In response to this signal, the arrhythmia detector 208 may commence arrhythmia detection for a defined period of time (e.g., five minutes).

In FIG. 2, the arrhythmia detector 208 processes cardiac signals sensed by a cardiac sense circuit 206. The cardiac sense circuit 206 may comprise, for example, one or more implantable leads, one or more sense amplifiers, and an intracardiac electrogram ("IEGM") processing component. Examples of these components are described in more detail below in conjunction with FIGS. 5 and 6. Also, in cases where activity sensing is based at least in part on sensed cardiac signals (e.g., for heart rate, QT interval, or respiration component sensing), the cardiac sensing circuit 206 may comprise at least a portion of the activity sensing circuit 202 of FIG. 2.

In some cases ischemia detection may be employed in conjunction with post-exercise arrhythmia detection. Cardiac ischemia is a condition whereby heart tissue does not receive adequate amounts of oxygen and is usually caused by the narrowing or blockage of an artery leading to heart tissue. If sufficiently severe, cardiac ischemia results in an acute myocardial infarction, also referred to as a heart attack.

As will be discussed in more detail below in conjunction with FIGS. 3A and 3B, an ischemic condition of a patient may be considered in combination with the occurrence of post-exercise arrhythmia to provide more effective treatment for the patient. For example, diagnostics provided by an implantable device may be enhanced by correlating post-exercise arrhythmias with the ischemic status of the patient during one or more monitoring periods (e.g., post-exercise only, or during exercise and post-exercise). As one specific example, in some cases more post-exercise arrhythmias may occur at a certain level of exercise when ischemia (e.g., a certain degree of ischemia) is present than when the ischemia is not present. As another example, in some cases post-exercise arrhythmia may be prognostic (or more prognostic) of a cardiac condition in the presence of ischemia (e.g., a certain degree of ischemia) but may not be prognostic in the absence of ischemia. Thus, a decision as to whether to detect post-exercise arrhythmia or act on any detected post-exercise arrhythmia may be based on the current ischemic condition of the patient. As another example, the detection of post-exercise arrhythmia in combination with ischemia may affect how the ischemia is treated.

The apparatus 200 may therefore include an ischemia detector 210 that is configured to monitor cardiac signals (e.g., as provided by the cardiac sense circuit 206) or other types of signals to determine the ischemic condition of the patient. As discussed in more detail below, the ischemic condition may be monitored during the post-exercise time period, during some other time period or time periods, or during some combination of these time periods.

Ischemia may be detected in different ways in different implementations. For example, in some cases the ischemia detector 210 may employ ST monitoring. Here, ischemia may be indicated by a change in the level of the ST segment (e.g., ST segment depression). Thus, the ischemia detector 210 may analyze IEGM data acquired from sensed cardiac signals or may analyze other signals that are indicative of ischemia.

As represented by block 108 of FIG. 1, in some implementations the arrhythmia detector 208 may compare a detected post-exercise arrhythmia with an arrhythmia threshold to determine whether the post-exercise arrhythmia warrants some form of action being taken (e.g., an adjustment in therapy). For example, in some cases post-exercise arrhythmia of a certain type, frequency, quantity, or severity may not be prognostic of a cardiac condition. Hence, it may be desirable to ignore such post-exercise arrhythmia or take a different action than the action taken for post-exercise arrhythmia that meet or exceed the arrhythmia threshold.

The arrhythmia threshold may take different forms in different implementations. For example, the arrhythmia threshold may relate to a type of arrhythmia, a frequency of arrhythmias, a severity of an arrhythmia, or some combination of these or other factors that are used to determined whether post-exercise arrhythmia is clinically actionable.

As represented by block 110 of FIG. 1, in the event post-exercise arrhythmia is detected (e.g., post-exercise arrhythmia of a given type and/or severity is detected), a corresponding indication of the post-exercise arrhythmia may be generated. For example, in some cases data and/or alerts may be provided to a physician. In some cases an implantable device generates a warning signal for alerting the patient or automatically delivers therapy. A warning signal may include, for example, a "tickle warning" signal applied to subcutaneous tissue and/or a short-range telemetry warning signal transmitted to a warning device that is external to the patient. The delivery of therapy in response to post-exercise arrhythmia depends upon the capabilities of the implantable device. In one example, if the implantable device is equipped with a drug pump, appropriate medications may be administered in response to a particular medical condition. If the implantable device includes cardiac stimulation (e.g., pacing and/or shocking) capability, the stimulation parameters may be adjusted in response to a particular medical condition.

In the example of FIG. 2, an indication generator 212 may perform the operations of block 110. For example, the indication generator 212 may receive information indication of the post-exercise arrhythmia from the arrhythmia detector 208 to generate an indication that is used to determine the appropriate therapy to be prescribed for the patient. In addition, in implementations where ischemia is also monitored, the indication generator 212 may generate the indication (or a different indication) based on information indicative of ischemia received from the ischemia detector 210.

Such an indication may take various forms. In some cases the indication may comprise IEGM data that corresponds to the times when the post-exercise arrhythmia (and optionally ischemia) occurred. In some cases the indication may comprise information that characterizes the post-exercise arrhythmia (and optionally ischemia). For example, such information may indicate the frequency and severity of the arrhythmia (and optionally ischemia) event. As discussed above, in some cases the indication may comprise an alert signal generated by an implantable device. In some cases the indication may comprise a trigger that changes how/whether an implantable device monitors or reports cardiac conditions.

A physician may obtain data and/or an alert from an implantable device via interrogation with a programmer, via remote interrogation, or in some other manner. This data may include, for example, logs of events, trends of events (e.g., whether the patient is having progressively more or fewer post-exercise arrhythmias over time), electrocardiograms (e.g., IEGMs), diagnostic counters, and so on.

Based on this data and/or on an alert, a physician may determine the appropriate therapy to prescribe for the patient. For example, the physician may elect to perform a stress test, prescribe drugs or change the drugs that are currently prescribed, change the operating parameters of an implanted device, or determine that a patient should be provided with a different type of implanted device. Advantageously, by regularly monitoring for post-exercise arrhythmia via an implantable device, patients that are potentially at high-risk of having a worsening cardiac condition may be readily identified without requiring that the patient undergo formal exercise testing on a routine basis. In particular, the teaching herein may be beneficially employed to identify pacemaker patients (e.g., who have not yet been designated as being high risk candidates for an implantable cardioverter defibrillator) who may benefit from an upgrade to an implantable cardioverter defibrillator.

With the above overview in mind, additional details relating to detecting post-exercise arrhythmias and other operations that may be employed in conjunction with such detection will now be described with reference to the flowchart of FIGS. 3A and 3B. In this example, a patient is considered to be exercising if his or her activity level is greater than or equal to an exercise threshold. In addition, this example illustrates that therapy for a patient may be prescribed based on post-exercise arrhythmia and other events such as, for example, arrhythmia and/or ischemia detected during exercise. In other words, diagnostics similar to those discussed above at block 106 may be recorded for events that occur during and/or before the exercise period to assist in the treatment of a patient.

Figure 3A:
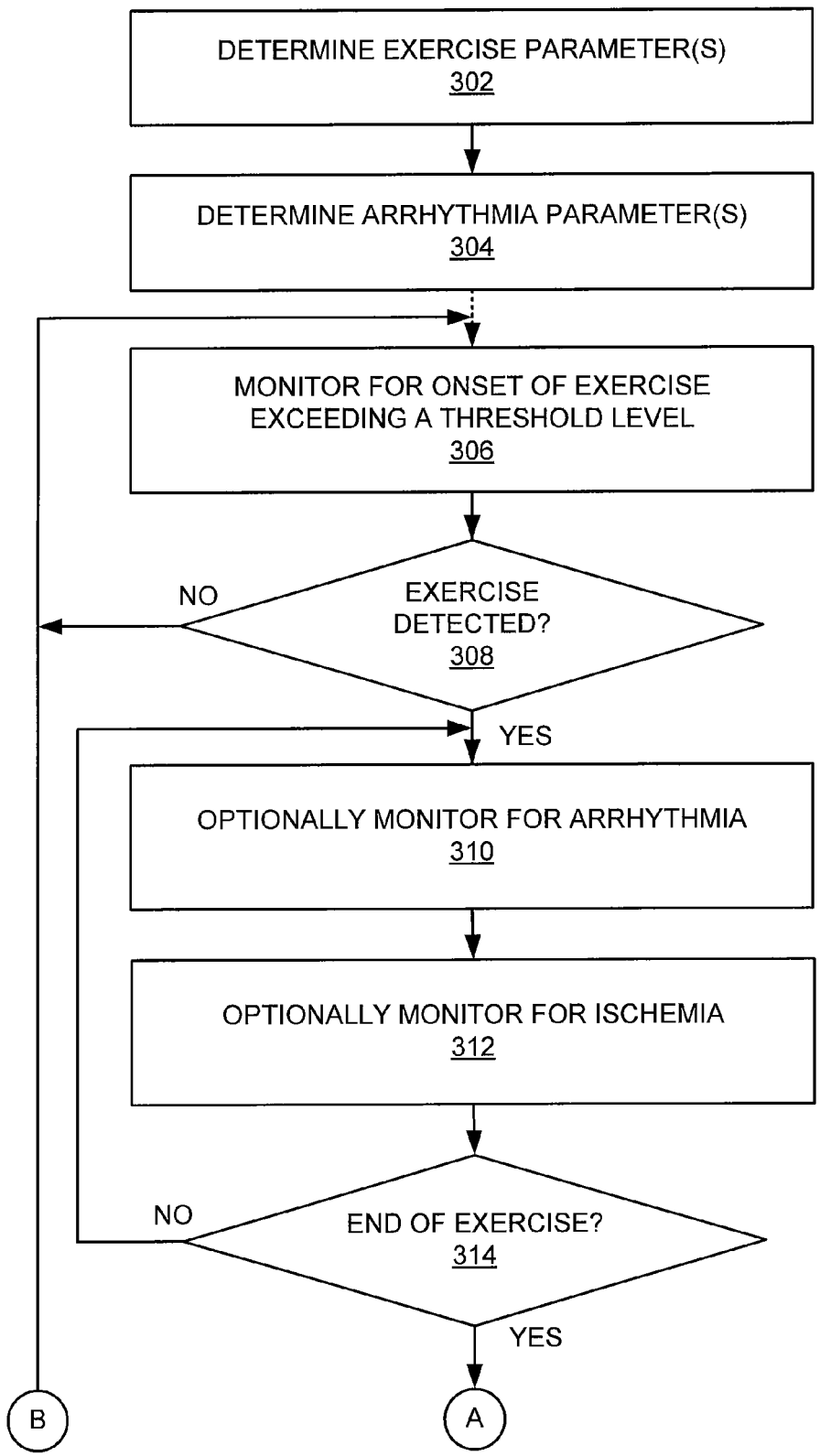
FIG. 3 is a simplified flowchart of an embodiment of operations that may be performed to detect post-exercise arrhythmia.

As represented by block 302 of FIG. 3A, at some point in time one or more exercise parameters may be determined for use in monitoring post-exercise arrhythmia. These exercise parameters may include, for example, one or more exercise thresholds as described above in conjunction with block 104. In some aspects an exercise threshold may be defined to be equivalent in prognostic ability to exercise testing. In this way, an implantable device may provide monitoring that may not otherwise be done or that would otherwise have to be performed during in-clinic stress testing which is relatively expensive and inconvenience for a patient. Once a given parameter is determined, the parameter may be stored in (e.g., programmed into) data memory of an implantable device.

An exercise parameter may be determined in various ways. In some cases an exercise parameter may be defined based on monitoring of a patient that is performed in a clinical or other comparable setting. For example, a patient may be subjected to a stress test or some other suitable test whereby exercise-related signals (e.g., acceleration, heart rate, respiration rate, etc.) are recorded along with cardiac-related signals (e.g., to detect arrhythmia and ischemia). In this way, the level of exercise that tends to result in post-exercise arrhythmia (optionally in conjunction with ischemia) that is prognostic of a cardiac condition may be determined. This information is then used to define one or more exercise thresholds. It should be appreciated that similar information may be determined in other ways. For example, in some cases an implantable device may be configured to monitor exercise-related signals and cardiac-related signals, whereby this information is used (e.g., uploaded to an external diagnostic device and/or processed by the implantable device) to determine the exercise threshold(s). Thus, in some cases an implantable device may be configured to automatically modify a threshold (e.g., based on whether post-exercise arrhythmia is being detected). In addition, in some cases an exercise parameter may be determined based on patient group information. For example, an exercise threshold may be defined by determining and exercise activity level (e.g., an average level) that is relatively prognostic of post-exercise arrhythmia for a group of patients (e.g., where groups of patients may be classified based on cardiac condition, age, and so on). As a specific example, in some cases it may be determined that a heart rate of 70% of a maximum predicted heart rate is prognostic for all patients (or all patients of a certain class of patients). However, in some cases it may be determine that for some patients a heart rate of 80% of a maximum predicted heart rate is prognostic.

As represented by block 304, one or more arrhythmia parameters also may be determined for use in monitoring post-exercise arrhythmia. These arrhythmia parameters may include, for example, one or more arrhythmia thresholds as described above in conjunction with block 108. As above, once a given parameter is determined, the parameter may be stored in (e.g., programmed into) data memory of an implantable device.

An arrhythmia parameter may be determined in various ways. In a similar manner as discussed above, an arrhythmia parameter may be defined based on clinical measurements for a particular patient, measurements for groups of patients, measurements by an implantable device, and so on. For example, historical patient information (e.g., from a sampling of patients) may be used to identify the post-exercise arrhythmia (e.g., type and/or severity) that are likely prognostic of a cardiac condition. This information may then be used to define one or more arrhythmia thresholds that are used, in turn, to determine whether to report an indicated arrhythmia as described below.

Referring again to FIGS. 3A and 3B, blocks 306-328 describe several operations that may be performed on a repeated basis to monitor post-exercise arrhythmia and adapt therapy for a patient based on detected post-exercise arrhythmia. For example, an implantable device may be configured to continuously or regularly monitor exercise-related signals and cardiac-related signals and, as appropriate, upload a report indicative of any detected post-exercise arrhythmia to an external device.

As represented by blocks 306 and 308, the implantable device monitors for the onset of exercise and determines whether the exercise exceeds an exercise threshold. Thus, at block 306 the implantable device may monitor signals from an accelerometer (e.g., located within the implantable device or elsewhere), from one or more implantable cardiac leads, from other sensors, or from some combination thereof and measure the intensity of the exercise. At block 308 the implantable device may compare these signals to an exercise threshold (e.g., as defined at block 302) as described above at blocks 102 and 104.

As represented by blocks 310 and 312, in the event exercise is detected, the implantable device may optionally monitor for arrhythmia and/or ischemia during exercise (e.g., on a continual or regular basis). For example, in some cases the presence of post-exercise arrhythmia in conjunction with arrhythmia and/or ischemia events that occur during exercise may be prognostic of a medical condition (e.g., more prognostic than post-exercise arrhythmia considered in isolation). The implantable device may monitor for these conditions in the same manner it monitors for similar conditions at other times. Thus, the implantable device may, for example, analyze IEGM data (e.g., acquired in conjunction with pacing operations) to detect arrhythmia and ischemia events.

It should be appreciated that arrhythmia and ischemia may be monitored at other times. For example, these conditions may be continuously monitored, whereby information regarding detected arrhythmia and ischemia may be collected irrespective of whether the patient is exercising.

As represented by block 314, the implantable device detects the end of exercise. For example, the implantable device may continue monitoring exercise-related signals once they are detected at block 308 to determine when the patient ceases exercising (e.g., the patient's exercise level drops below the threshold level).

It should be appreciated that the detection of exercise may be achieved in different ways in different implementations. For example, in some implementations an implantable device may initially detect the onset of exercise (e.g., any level of exercise), then commence measuring the intensity of the exercise until the end of exercise is detected. Once the exercise has ended, the implantable device may then compare the intensity and duration of the exercise with one or more thresholds to determine whether to monitor for post-exercise arrhythmia.

Figure 3B:
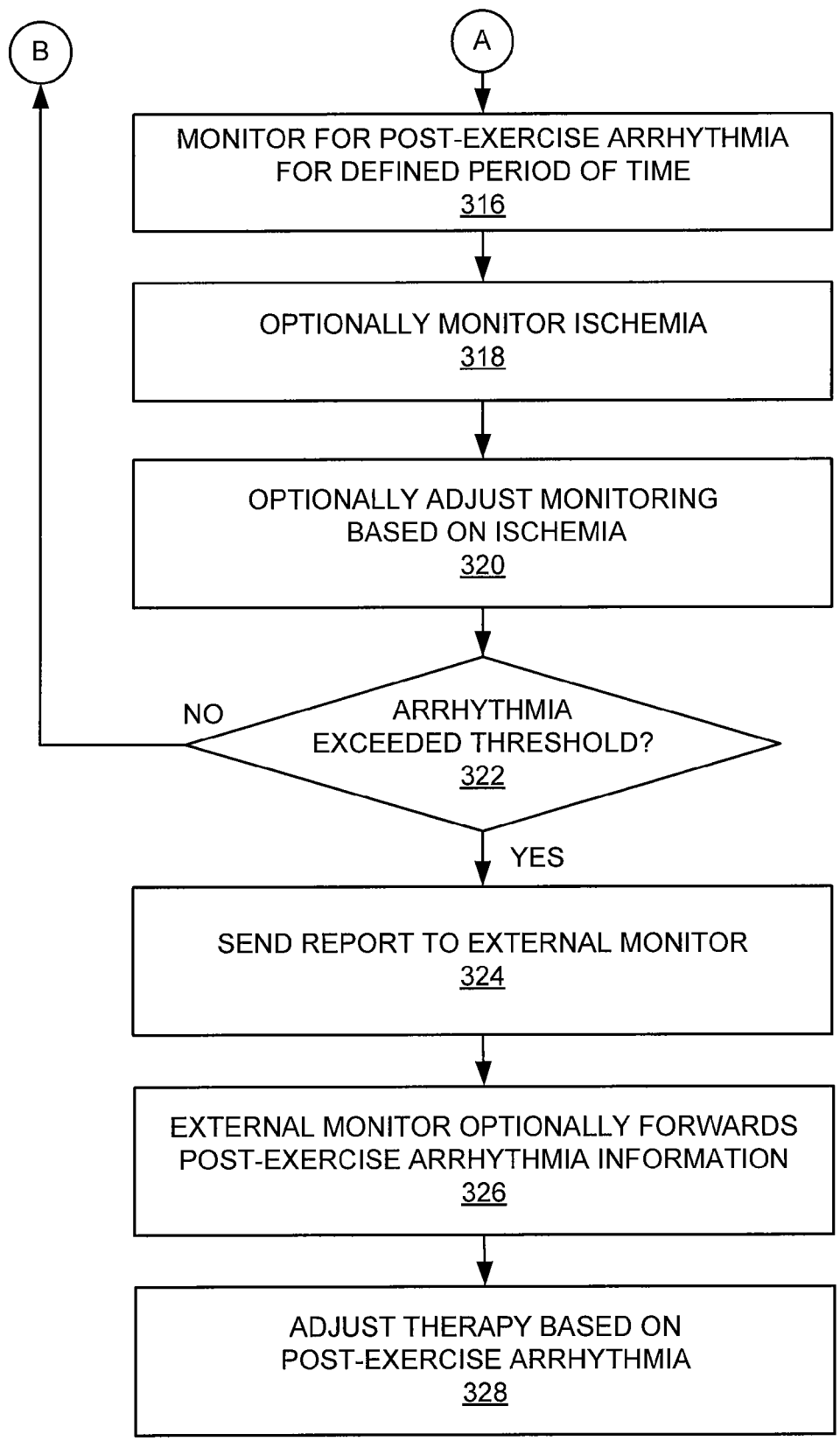

In any event, as represented by block 316 of FIG. 3B, the implantable device commences arrhythmia monitoring after an appropriate exercise episode has ended. The implantable device may conduct this monitoring for a defined period of time (e.g., 5 minutes), until an event occurs (e.g., a certain quantity of post-exercise arrhythmia are detected), or until the monitoring is terminated for some other reason. Here, the determination of how long post-exercise arrhythmia is monitored may be a programmable device parameter. For example, based on clinical studies or monitored cardiac events, it may be determined that post-exercise arrhythmia should be monitored over longer or short periods of time in different patients. The implantable device may monitor for post-exercise arrhythmia in same manner it monitors for similar arrhythmias at other times. Thus, the implantable device may, for example, analyze IEGM data or other suitable signals (e.g., as discussed above at block 106).

As represented by block 318, the implantable device also may optionally monitor for ischemia after exercise. For example, the implantable device may concurrently monitor for ischemia during the same period of time that the device is monitoring for post-exercise arrhythmia at block 316.

As represented by block 320, in some implementations the post-exercise arrhythmia monitoring may be adapted based on detected ischemia. For example, in some cases the implantable device (e.g., the arrhythmia detector 208) may determine whether to monitor for post-exercise arrhythmia based on whether ischemia is detected. Here, post-exercise arrhythmia monitoring may be triggered based on a detection of ischemia (e.g., a certain level of ischemia) before exercise, during exercise, after exercise, or some combination thereof. For example, post-exercise arrhythmia monitoring may be enabled only if ischemia is detected. In some cases the implantable device may adapt how it monitors for post-exercise arrhythmia based on whether ischemia is detected. For example, the arrhythmia detector 208 may adjust the arrhythmia threshold if ischemia is detected (e.g., whereby a lower level of arrhythmia activity may trigger a report if ischemia is present as opposed to when ischemia is not present).

As represented by block 322, in some implementations the implantable device (e.g., the indication generator 212) may condition the reporting of post-exercise arrhythmia based on whether the post-exercise arrhythmia exceed a defined threshold (e.g., as defined at block 304) as mentioned above at block 108. Thus, this decision may be made once the post-exercise arrhythmia monitoring of block 316 concludes (e.g., at the end of the defined period of time).

As represented by block 324, if post-exercise arrhythmia was detected, the implantable device may send a report to an external monitor. For example, the implantable device may generate information (e.g., diagnostic information) pertaining to any detected arrhythmia for subsequent review by a physician or other clinician. This information may then be transmitted from the implanted device to an external device (e.g., a bedside monitor, external programmer, or other device). For example, the external device may interrogate the implantable device at regular intervals or information may be uploaded based on some trigger event. The external device may further process the information and display the information or send the information to another device (e.g., a web server) from which the information may be accessed (block 326).

In some aspects, the information to be uploaded from an implantable device may be specified. For example, a cardiologist may wish to analyze any information dealing with heart failure conditions (e.g., post-exercise arrhythmia and ischemia data) while an electrophysiologist may wish to analyze information relating to arrhythmias and the implantable device. Hence, the implantable device and/or the external device may be configured to upload one type of information when sending a report for a one user and upload another type of information when sending a report for another user. Here, a decision to upload information may be predicated on whether a particular condition (e.g., specified by the physician) has been met. For example, post-exercise arrhythmia information may be uploaded if a post-exercise arrhythmia has occurred or if a certain number of post-exercise arrhythmias have occurred.

As discussed above, in some implementations a decision to report a detected post-exercise arrhythmia may be based on the ischemic condition of the patient. For example, in some cases an implantable device (e.g., the indication generator 212) may only send the report if the patient is determined to be ischemic (e.g., to a certain degree).

Figure 4:
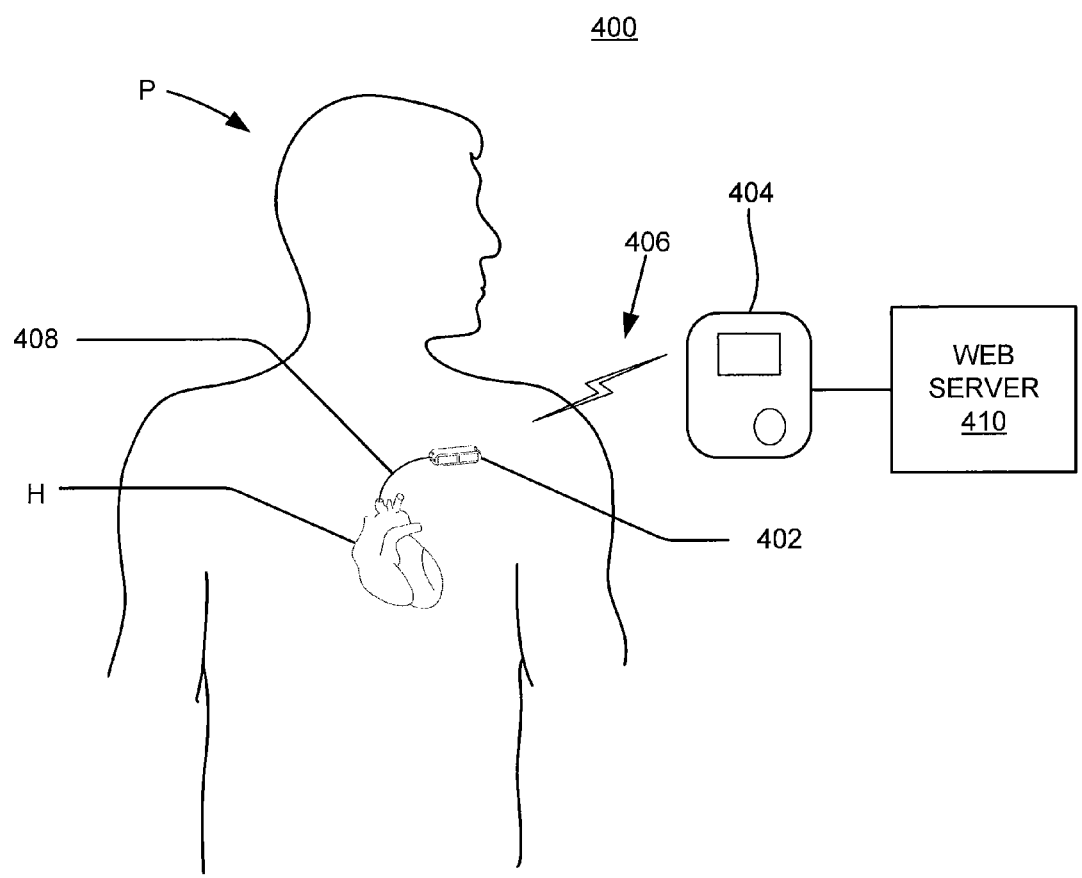
FIG. 4 is a simplified diagram of a medical system including an implantable medical device and an external monitor device.

FIG. 4 illustrates a simplified diagram of a device 402 (implanted within a patient P) that communicates with a device 404 that is located external to the patient P. The implanted device 402 and the external device 404 may communicate with one another via a wireless communication link 406 (as represented by the illustrated symbol).

In this example, the implanted device 402 is an implantable cardiac device including one or more leads 408 that are routed to the heart H of the patient P. For example, the implanted device 402 may be a pacemaker, an implantable cardioverter defibrillator, or some other similar device. It should be appreciated, however, that the implanted device 402 may take other forms.

The external device 404 also may take various forms. For example, the external device 404 may be a base station, a programmer, a home safety monitor, a personal monitor, a follow-up monitor, a wearable monitor, or some other type of device that is configured to communicate with the implanted device 402.

In a typical embodiment, the communication link 406 is an RF link. In some embodiments the communication link 406 may operate within the medical implant communication service ("MICS") band. It should be appreciated, however, that the teachings herein may be employed in conjunction with other RF bands. In some embodiments the communication link 406 may take other forms including, for example, an inductive telemetry link.

The communication link 406 may be used to transfer information between the devices 402 and 404 in conjunction with various applications such as remote home-monitoring, clinical visits, data acquisition, remote follow-up, and portable or wearable patient monitoring/control systems. For example, when information needs to be transferred between the devices 402 and 404, the patient P moves into a position that is relatively close to the external device 404, or vice versa.

As mentioned above, an external device may send information it receives from an implanted device to another device (e.g., that may provide a more convenient means for a physician to review the information). For example, the external device 404 may send the information to a web server 410. In this way, the physician may remotely access the information (e.g., by accessing a website).

As represented by block 328 of FIG. 3B, a physician may review the information uploaded from the implantable device to determine whether the arrhythmia is "clinically actionable" (i.e. to determine whether medical intervention is warranted). For example, the information might indicate a change in duration and/or severity of arrhythmia events over time. If the arrhythmia worsens, medical intervention may be necessary.

As mentioned above, in some implementations cardiac ischemia diagnostics may be considered in combination with post-exercise arrhythmias diagnostics. In one example, the diagnostics are generated by a pacemaker or other implantable medical device and then transmitted to an external system for review by a physician. In some aspects the diagnostics may allow the physician to make a more informed judgment as to whether episodes of cardiac ischemia are clinically actionable.

In another example, the implantable device may generate diagnostics relating the post-exercise arrhythmia and cardiac ischemia events, and then control at least one device function based on the diagnostics. For example the implantable device may control the recording of the diagnostics in memory, control the generation of warning signals, or control the delivery of pacing or other therapy. The implantable device also may evaluate the relative severity of individual episodes of cardiac ischemia and also track the time of day when post-exercise arrhythmia and episodes of cardiac ischemia occur.

The implantable device may generate and record diagnostic information that tracks and distinguishes arrhythmia events based on, for example, arrhythmia type (e.g., ventricular vs. supraventricular), duration (lone, couplet, runs of 3-5 beats, runs of 6-10 beats, etc.), the rate of events, the presence or absence of ischemia, the severity of ischemia, the time of day, or some combination of these factors. Changes over time in these parameters also may be tracked such as: changes in the rate at which events occur; changes in the ratio of lone events to runs of events; changes in the ratio of arrhythmia events occurring during episodes of ischemia as compared to events occurring during episodes without ischemia; and changes in the durations of individual events, such as the durations of episodes of non-sustained SVT. The diagnostics may be transmitted to an external device for physician review as discussed herein. Alternatively, raw data detected by the implanted device is transmitted to the external device, which generates the ischemia diagnostics therein. Also as discussed above, a physician may control the specific information to be displayed so as to highlight information that he or she finds particularly helpful in deciding whether the ischemia is clinically actionable. In this regard, minor arrhythmias may be harbingers of sustained, potentially lethal arrhythmias. Hence, any information pertaining to the association of arrhythmia events with ischemic episodes may make clinical intervention to address the ischemia (e.g., angioplasty, coronary artery bypass graft, etc.) more urgent. Similarly, if the ischemic events only occur when tachycardias occur, then the physician may choose to adjust prescribed medications, upgrade from a pacer to an ICD, etc., to address the tachycardias so as to, in turn, reduce ischemia within the patient.

In some implementations, cardiac ischemia diagnostics are generated that take into account whether episodes of arrhythmia precede episodes of cardiac ischemia or follow the ischemia (i.e., whether arrhythmias are pre-ischemia or post-ischemia). A pre-ischemia arrhythmia is an arrhythmia that begins prior to the onset of an episode of ischemia. A post-ischemia arrhythmia is an arrhythmia that beginnings following the onset of an episode of ischemia, and thus includes arrhythmias that begin sometime during an ischemia episode. Pre-ischemia arrhythmias may also be referred to as "pre-ischemia onset arrhythmias." Likewise, post-ischemia arrhythmias may also be referred to as "post-ischemia-onset arrhythmias." The onset of an episode of ischemia may be defined as the point at which a parameter indicative of ischemia (e.g. ST segment deviation) crosses a detection threshold.

Figure 5:
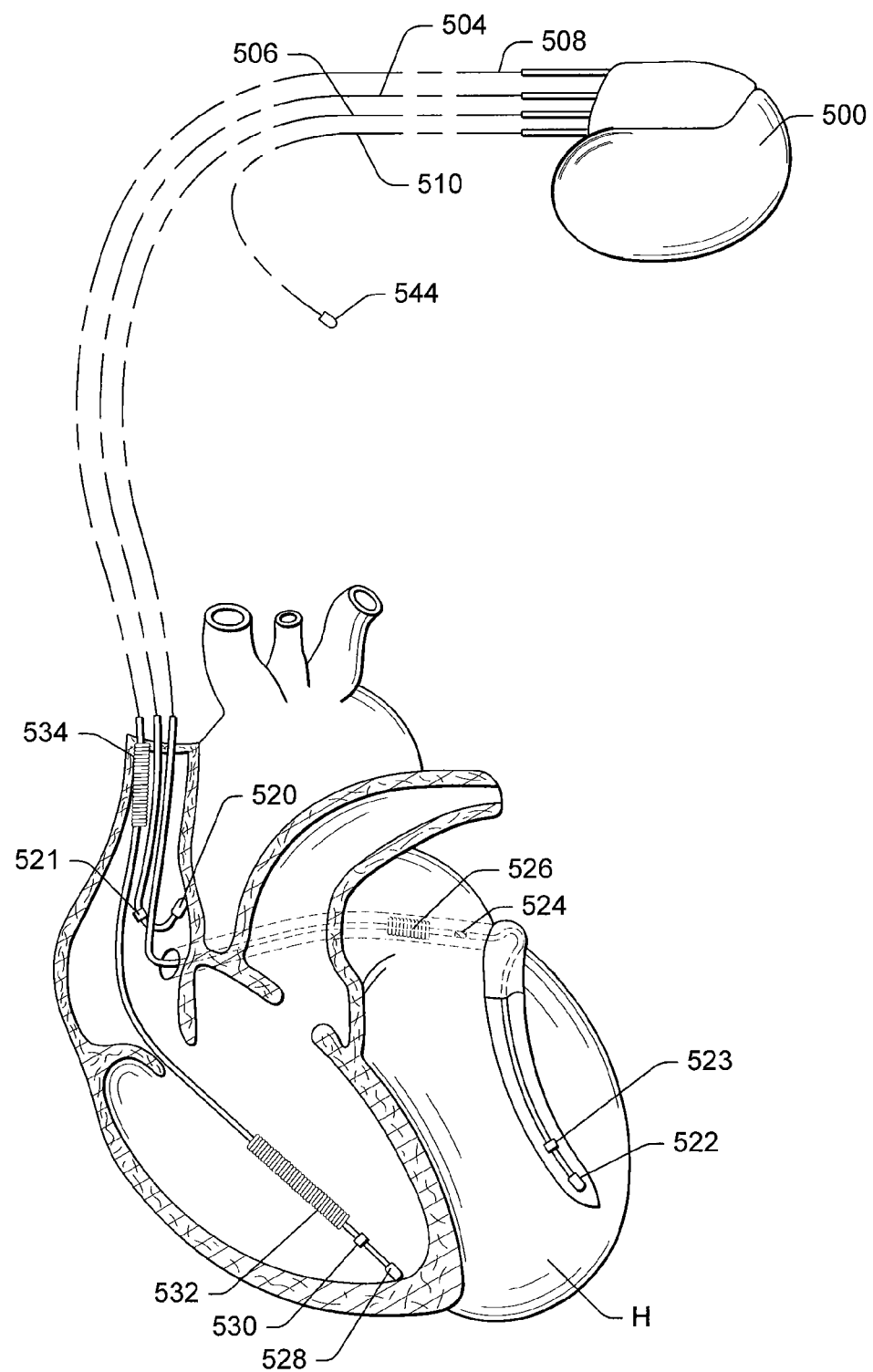
FIG. 5 is a simplified diagram of an embodiment of an implantable stimulation device in electrical communication with one or more leads implanted in a patient's heart for sensing conditions in the patient, delivering therapy to the patient, or providing some combination thereof.
Figure 6:
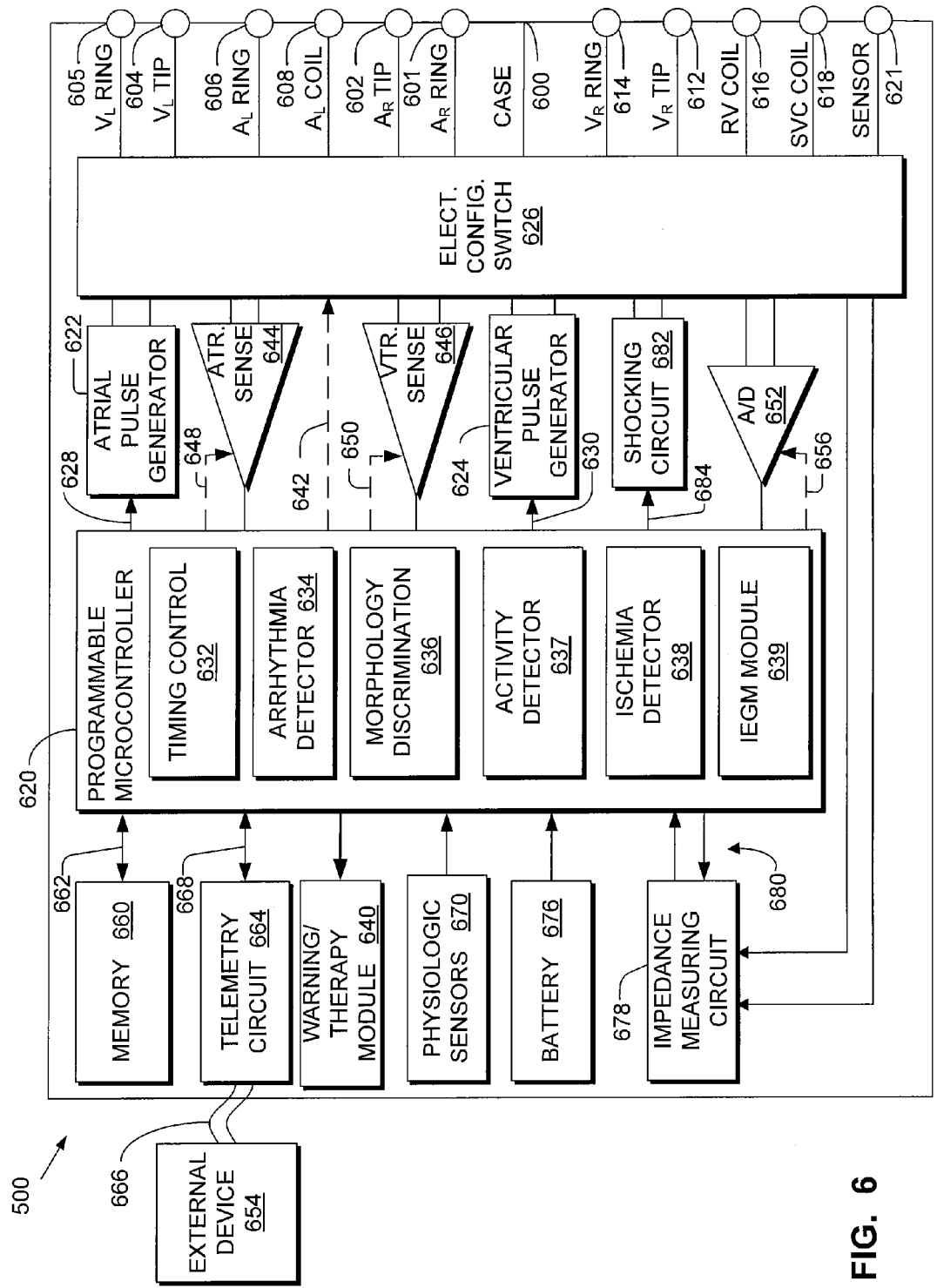
FIG. 6 is a simplified functional block diagram of an embodiment of an implantable cardiac device, illustrating basic elements that may be configured to sense conditions in the patient, deliver therapy to the patient, or provide some combination thereof.

Referring now to FIGS. 5 and 6, an example of an implantable cardiac device (e.g., a stimulation device such as an implantable cardioverter defibrillator, a pacemaker, etc.) that may be implemented in accordance with the teachings herein will be described. It is to be appreciated and understood that other cardiac devices, including those that are not necessarily implantable, may be used and that the description below is given, in its specific context, to assist the reader in understanding, with more clarity, the embodiments described herein.

FIG. 5 shows an exemplary implantable cardiac device 500 in electrical communication with a patient's heart H by way of three leads 504, 506, and 508, suitable for delivering multi-chamber stimulation and shock therapy. To sense atrial cardiac signals and to provide right atrial chamber stimulation therapy, the device 500 is coupled to an implantable right atrial lead 504 having, for example, an atrial tip electrode 520, which typically is implanted in the patient's right atrial appendage or septum. FIG. 5 also shows the right atrial lead 504 as having an optional atrial ring electrode 521.

To sense left atrial and ventricular cardiac signals and to provide left chamber pacing therapy, the device 500 is coupled to a coronary sinus lead 506 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 506 is designed to receive atrial and ventricular cardiac signals and to deliver left ventricular pacing therapy using, for example, a left ventricular tip electrode 522 and, optionally, a left ventricular ring electrode 523; provide left atrial pacing therapy using, for example, a left atrial ring electrode 524; and provide shocking therapy using, for example, a left atrial coil electrode 526 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 500 is also shown in electrical communication with the patient's heart H by way of an implantable right ventricular lead 508 having, in this implementation, a right ventricular tip electrode 528, a right ventricular ring electrode 530, a right ventricular (RV) coil electrode 532 (or other electrode capable of delivering a shock), and a superior vena cava (SVC) coil electrode 534 (or other electrode capable of delivering a shock). Typically, the right ventricular lead 508 is transvenously inserted into the heart H to place the right ventricular tip electrode 528 in the right ventricular apex so that the RV coil electrode 532 will be positioned in the right ventricle and the SVC coil electrode 534 will be positioned in the superior vena cava. Accordingly, the right ventricular lead 508 is capable of sensing or receiving cardiac signals, and delivering stimulation in the form of pacing and shock therapy to the right ventricle.

The device 500 is also shown in electrical communication with a lead 510 including one or more components 544 such as a physiologic sensor (e.g., one or more activity sensors). The component 544 may be positioned in, near, or remote from the heart.

It should be appreciated that the device 500 may connect to leads other than those specifically shown. In addition, the leads connected to the device 500 may include components other than those specifically shown. For example, a lead may include other types of electrodes, sensors or devices that serve to otherwise interact with a patient or the surroundings.

FIG. 6 depicts an exemplary, simplified block diagram illustrating sample components of the device 500. The device 500 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 600 for the device 500 is often referred to as the "can", "case" or "case electrode", and may be programmably selected to act as the return electrode for all "unipolar" modes. The housing 600 may further be used as a return electrode alone or in combination with one or more of the coil electrodes 526, 532 and 534 for shocking purposes. Housing 600 further includes a connector (not shown) having a plurality of terminals 601, 602, 604, 605, 606, 608, 612, 614, 616 and 618 (shown schematically and, for convenience, the names of the electrodes to which they are connected are shown next to the terminals). The connector may be configured to include various other terminals (e.g., terminal 621 coupled to a sensor or some other component) depending on the requirements of a given application.

To achieve right atrial sensing and pacing, the connector includes, for example, a right atrial tip terminal (AR TIP) 602 adapted for connection to the right atrial tip electrode 520. A right atrial ring terminal (AR RING) 601 may also be included and adapted for connection to the right atrial ring electrode 521. To achieve left chamber sensing, pacing, and shocking, the connector includes, for example, a left ventricular tip terminal (VL TIP) 604, a left ventricular ring terminal (VL RING) 605, a left atrial ring terminal (AL RING) 606, and a left atrial shocking terminal (AL COIL) 608, which are adapted for connection to the left ventricular tip electrode 522, the left ventricular ring electrode 523, the left atrial ring electrode 524, and the left atrial coil electrode 526, respectively.

To support right chamber sensing, pacing, and shocking, the connector further includes a right ventricular tip terminal (VR TIP) 612, a right ventricular ring terminal (VR RING) 614, a right ventricular shocking terminal (RV COIL) 616, and a superior vena cava shocking terminal (SVC COIL) 618, which are adapted for connection to the right ventricular tip electrode 528, the right ventricular ring electrode 530, the RV coil electrode 532, and the SVC coil electrode 534, respectively.

At the core of the device 500 is a programmable microcontroller 620 that controls the various modes of stimulation therapy. As is well known in the art, microcontroller 620 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 620 includes the ability to process or monitor input signals (data or information) as controlled by a program code stored in a designated block of memory. The type of microcontroller is not critical to the described implementations. Rather, any suitable microcontroller 620 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 6 also shows an atrial pulse generator 622 and a ventricular pulse generator 624 that generate pacing stimulation pulses for delivery by the right atrial lead 504, the coronary sinus lead 506, the right ventricular lead 508, or some combination of these leads via an electrode configuration switch 626. It is understood that in order to provide stimulation therapy in each of the four chambers of the heart, the atrial and ventricular pulse generators 622 and 624 may include dedicated, independent pulse generators, multiplexed pulse generators, or shared pulse generators. The pulse generators 622 and 624 are controlled by the microcontroller 620 via appropriate control signals 628 and 630, respectively, to trigger or inhibit the stimulation pulses.

Microcontroller 620 further includes timing control circuitry 632 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 620 further includes an arrhythmia detector 634. The arrhythmia detector 634 may be utilized by the device 500 for determining desirable times to administer various therapies. The arrhythmia detector 634 may be implemented, for example, in hardware as part of the microcontroller 620, or as software/firmware instructions programmed into the device 500 and executed on the microcontroller 620 during certain modes of operation.

Microcontroller 620 also may include a morphology discrimination module 636, a capture detection module (not shown) and an auto sensing module (not shown). These modules are optionally used to implement various exemplary recognition algorithms or methods. The aforementioned components may be implemented, for example, in hardware as part of the microcontroller 620, or as software/firmware instructions programmed into the device 500 and executed on the microcontroller 620 during certain modes of operation.

The electrode configuration switch 626 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 626, in response to a control signal 642 from the microcontroller 620, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 644 and ventricular sensing circuits (VTR. SENSE) 646 may also be selectively coupled to the right atrial lead 504, coronary sinus lead 506, and the right ventricular lead 508, through the switch 626 for detecting the presence of cardiac activity in each of the four chambers of the heart. Accordingly, the atrial and ventricular sensing circuits 644 and 646 may include dedicated sense amplifiers, multiplexed amplifiers, or shared amplifiers. Switch 626 determines the "sensing polarity" of the cardiac signal by selectively closing the appropriate switches, as is also known in the art. In this way, the clinician may program the sensing polarity independent of the stimulation polarity. The sensing circuits (e.g., circuits 644 and 646) are optionally capable of obtaining information indicative of tissue capture.

Each sensing circuit 644 and 646 preferably employs one or more low power, precision amplifiers with programmable gain, automatic gain control, bandpass filtering, a threshold detection circuit, or some combination of these components, to selectively sense the cardiac signal of interest. The automatic gain control enables the device 500 to deal effectively with the difficult problem of sensing the low amplitude signal characteristics of atrial or ventricular fibrillation.

The outputs of the atrial and ventricular sensing circuits 644 and 646 are connected to the microcontroller 620, which, in turn, is able to trigger or inhibit the atrial and ventricular pulse generators 622 and 624, respectively, in a demand fashion in response to the absence or presence of cardiac activity in the appropriate chambers of the heart. Furthermore, as described herein, the microcontroller 620 is also capable of analyzing information output from the sensing circuits 644 and 646, a data acquisition system 652, or both. This information may be used to determine or detect whether and to what degree tissue capture has occurred and to program a pulse, or pulses, in response to such determinations. The sensing circuits 644 and 646, in turn, receive control signals over signal lines 648 and 650, respectively, from the microcontroller 620 for purposes of controlling the gain, threshold, polarization charge removal circuitry (not shown), and the timing of any blocking circuitry (not shown) coupled to the inputs of the sensing circuits 644 and 646 as is known in the art.

For arrhythmia detection, the device 500 utilizes the atrial and ventricular sensing circuits 644 and 646 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 634 of the microcontroller 620 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 652. The data acquisition system 652 is configured (e.g., via signal line 656) to acquire intracardiac electrogram ("IEGM") signals or other signals, convert the raw analog data into a digital signal, and store the digital signals for later processing, for telemetric transmission to an external device 654, or both. For example, the data acquisition system 652 may be coupled to the right atrial lead 504, the coronary sinus lead 506, the right ventricular lead 508 and other leads through the switch 626 to sample cardiac signals across any pair of desired electrodes.

The data acquisition system 652 also may be coupled to receive signals from other input devices. For example, the data acquisition system 652 may sample signals from a physiologic sensor 670 or other components shown in FIG. 6 (connections not shown).

The microcontroller 620 is further coupled to a memory 660 by a suitable data/address bus 662, wherein the programmable operating parameters used by the microcontroller 620 are stored and modified, as required, in order to customize the operation of the device 500 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 652), which data may then be used for subsequent analysis to guide the programming of the device 500.

Advantageously, the operating parameters of the implantable device 500 may be non-invasively programmed into the memory 660 through a telemetry circuit 664 in telemetric communication via communication link 666 with the external device 654, such as a programmer, transtelephonic transceiver, a diagnostic system analyzer or some other device. The microcontroller 620 activates the telemetry circuit 664 with a control signal (e.g., via bus 668). The telemetry circuit 664 advantageously allows intracardiac electrograms and status information relating to the operation of the device 500 (as contained in the microcontroller 620 or memory 660) to be sent to the external device 654 through an established communication link 666.

The device 500 can further include one or more physiologic sensors 670. In some embodiments the device 500 may include a "rate-responsive" sensor that may provide, for example, information to aid in adjustment of pacing stimulation rate according to the exercise state of the patient. One or more physiologic sensors 670 (e.g., a pressure sensor) may further be used to detect changes in cardiac output, changes in the physiological condition of the heart, or diurnal changes in activity (e.g., detecting sleep and wake states). Accordingly, the microcontroller 620 responds by adjusting the various pacing parameters (such as rate, A-V Delay, V-V Delay, etc.) at which the atrial and ventricular pulse generators 622 and 624 generate stimulation pulses.

While shown as being included within the device 500, it is to be understood that a physiologic sensor 670 may also be external to the device 500, yet still be implanted within or carried by the patient. Examples of physiologic sensors that may be implemented in conjunction with the device 500 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 670 may optionally include one or more of components to help detect movement (via, e.g., a position sensor or an accelerometer) and minute ventilation (via an MV sensor) in the patient. Signals generated by the position sensor and MV sensor may be passed to the microcontroller 620 for analysis in determining whether to adjust the pacing rate, etc. The microcontroller 620 may thus monitor the signals for indications of the patient's position and activity status, such as whether the patient is climbing up stairs or descending down stairs or whether the patient is sitting up after lying down.

The device 500 additionally includes a battery 676 that provides operating power to all of the circuits shown in FIG. 6. For a device 500 which employs shocking therapy, the battery 676 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 676 also desirably has a predictable discharge characteristic so that elective replacement time can be detected. Accordingly, the device 500 preferably employs lithium or other suitable battery technology.

The device 500 can further include magnet detection circuitry (not shown), coupled to the microcontroller 620, to detect when a magnet is placed over the device 500. A magnet may be used by a clinician to perform various test functions of the device 500 and to signal the microcontroller 620 that the external device 654 is in place to receive data from or transmit data to the microcontroller 620 through the telemetry circuit 664.

The device 500 further includes an impedance measuring circuit 678 that is enabled by the microcontroller 620 via a control signal 680. The known uses for an impedance measuring circuit 678 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 500 has been implanted; measuring stroke volume; and detecting the opening of heart valves, etc. The impedance measuring circuit 678 is advantageously coupled to the switch 626 so that any desired electrode may be used.

In the case where the device 500 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 620 further controls a shocking circuit 682 by way of a control signal 684. The shocking circuit 682 generates shocking pulses of low (e.g., up to 0.5 J), moderate (e.g., 0.5 J to 10 J), or high energy (e.g., 11 J to 40 J), as controlled by the microcontroller 620. Such shocking pulses are applied to the patient's heart H through, for example, two shocking electrodes and as shown in this embodiment, selected from the left atrial coil electrode 526, the RV coil electrode 532 and the SVC coil electrode 534. As noted above, the housing 600 may act as an active electrode in combination with the RV coil electrode 532, as part of a split electrical vector using the SVC coil electrode 534 or the left atrial coil electrode 526 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 620 is capable of controlling the synchronous or asynchronous delivery of the shocking pulses.

As mentioned above, the device 500 may include several components that provide arrhythmia detection-related functionality as taught herein. For example, one or more of the switch 626, the sense circuits 644, 646, and the data acquisition system 652 may acquire cardiac signals that may used in the arrhythmia, ischemia, or activity detection operations discussed above, with reference to FIGS. 1-3B. The data described above may be stored in the data memory 660. In addition, a warning/therapy module 640 may be configured to generate warning signals upon arrhythmia detection and facilitate the administration of therapy.

The microcontroller 620 (e.g., a processor providing signal processing functionality) also may implement or support at least a portion of the arrhythmia detection-related functionality discussed herein. For example, the arrhythmia detector 634 may perform arrhythmia detection as described above with reference to FIGS. 1-3B. An activity detector 637 may perform activity detection as described above with reference to FIGS. 1-3B. An ischemia detector 638 may perform ischemia detection as described above with reference to FIGS. 1-3B. In addition, an IEGM module 639 may be used to acquire IEGM data that may be used by the above components.

It should be appreciated from the above that the various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. A method of detection for an implantable cardiac device, comprising:
    monitoring exercise by a patient; comparing the monitored exercise with an exercise threshold; detecting an end of the exercise;
    detecting arrhythmia during a period of time after the end of the exercise if the monitored exercise equals or exceeds the exercise threshold;
    comparing the detected arrhythmia with an arrhythmia threshold;
    generating an indication of post-exercise arrhythmia if the detected arrhythmia equals or exceeds the arrhythmia threshold; and
    adapting therapy for the patient based on the indication of post-exercise arrhythmia.

2. The method of claim 1, wherein the exercise threshold corresponds to a level of exercise that results in post-exercise arrhythmia data being prognostic of cardiovascular mortality.

3. The method of claim 1, wherein the arrhythmia threshold corresponds to an arrhythmia that is prognostic of cardiovascular mortality.

4. The method of claim 1, further comprising determining an ischemic condition of the patient, wherein the arrhythmia threshold is adapted based on the ischemic condition.

5. The method of claim 1, further comprising determining an ischemic condition of the patient, wherein the detection of the arrhythmia is based on the ischemic condition.

6. The method of claim 1, further comprising:
    determining an ischemic condition of the patient; and
    determining, based on the ischemic condition, whether to report the detected arrhythmia.

7. The method of claim 1, further comprising:
    determining an ischemic condition of the patient; and
    transmitting at least one indication of the detected arrhythmia and the determined ischemic condition to a monitor that is external to the patient.

8. The method of claim 1, wherein the detected arrhythmia comprises one or more ventricular contractions.

9. The method of claim 1, wherein the detected arrhythmia comprises sustained ventricular tachycardia.

10. The method of claim 1, wherein the detected arrhythmia comprises one or more atrial contractions.

11. An implantable cardiac device, comprising:
    an activity sensing circuit configured to monitor exercise by a patient;
    an exercise detector configured to compare the monitored exercise with an exercise threshold, and further configured to detect an end of the exercise;
    an arrhythmia detector configured to detect arrhythmia during a period of time after the end of the exercise if the monitored exercise equals or exceeds the exercise threshold;
    wherein the arrhythmia detector is further configured to compare the detected arrhythmia with an arrhythmia threshold, the apparatus further comprising;
    an indication generator configured to generate an indication of post-exercise arrhythmia if the detected arrhythmia equals or exceeds the arrhythmia threshold; and
    a therapy module configured to adapt therapy for the patient based on the indication of post-exercise arrhythmia.

12. The apparatus of claim 11, wherein the exercise threshold corresponds to a level of exercise that results in post-exercise arrhythmia data being prognostic of cardiovascular mortality.

13. The apparatus of claim 1, wherein the arrhythmia threshold corresponds to an arrhythmia that is prognostic of cardiovascular mortality.

14. The apparatus of claim 1, further comprising an ischemia detector configured to determine an ischemic condition of the patient, wherein the arrhythmia detector is further configured to adapt the arrhythmia threshold based on the ischemic condition.

15. The apparatus of claim 12, further comprising an ischemia detector configured to determine an ischemic condition of the patient, wherein the arrhythmia detector is further configured to detect the arrhythmia based on the ischemic condition.

16. The apparatus of claim 12, further comprising:
an ischemia detector configured to determine an ischemic condition of the patient; and
an indication generator configured to determine, based on the ischemic condition, whether to report the detected arrhythmia.

17. The apparatus of claim 11, further comprising:
an ischemia detector configured to determine an ischemic condition of the patient; and
an indication generator configured to transmit at least one indication of the detected arrhythmia and the determined ischemic condition to a monitor that is external to the patient.

18. The apparatus of claim 11, wherein the detected arrhythmia comprises one or more ventricular contractions, sustained ventricular tachycardia, or one or more atrial contractions.

* * * * *